United States Patent [19]

Kreidl et al.

[11] Patent Number: 4,956,007
[45] Date of Patent: Sep. 11, 1990

[54] NITRAMINODIARYL SULFOXIDE DERIVATIVES, PROCESS FOR THEIR PREPARATION AND PHARMACEUTICAL AND PESTICIDAL COMPOSITIONS CONTAINING THEM

[75] Inventors: János Kreidl; Péter Turcsányi; Béla Stefkó; Judit Mészáros née Brill; Erika Bogsch, all of Budapest, Hungary

[73] Assignee: Richter Gedeon Vegyeszeti Gyor Rt., Budapest, Hungary

[21] Appl. No.: 706,705

[22] Filed: Feb. 28, 1985

[30] Foreign Application Priority Data

Feb. 29, 1984 [HU] Hungary ................ 814/84

[51] Int. Cl.$^5$ ............. A01N 41/00; C07C 93/14
[52] U.S. Cl. ........................... 71/103; 71/121; 564/430
[58] Field of Search ............ 564/430, 398; 71/121, 71/103, 134

[56] References Cited

U.S. PATENT DOCUMENTS

| 3,506,767 | 4/1970 | Frick et al. ............ 564/430 X |
| 3,900,473 | 8/1975 | Diel et al. ............ 564/430 X |
| 4,034,107 | 7/1977 | King et al. ............ 424/309 |
| 4,105,797 | 8/1978 | Schneider et al. ........ 564/430 X |
| 4,122,089 | 10/1978 | Kimura et al. .......... 564/430 X |

FOREIGN PATENT DOCUMENTS

| 2462258 | 7/1976 | Fed. Rep. of Germany ...... 564/430 |
| 2549417 | 7/1976 | Fed. Rep. of Germany ...... 564/430 |
| 1156005 | 6/1969 | United Kingdom ............ 564/430 |

OTHER PUBLICATIONS

Chemical Abstracts, vol. 74, 53202b, (1971).

Primary Examiner—Robert V. Hines
Attorney, Agent, or Firm—Herbert Dubno; Jonathan Myers

[57] ABSTRACT

The invention relates to a new process for the preparation of nitraminodiaryl sulfoxide derivatives of the formula (I),

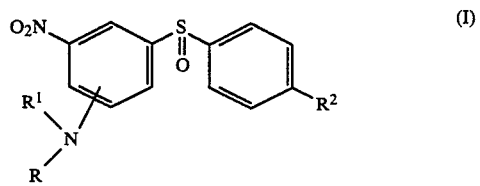

wherein
R and $R^1$ represent hydrogen or alkyl having from 1 to 6 carbon atoms, and
$R^2$ is hydrogen, halogen, alkyl having from 1 to 6 carbon atoms, alkoxy having from 1 to 6 carbon atoms, or phenyl or thiophenyl both optionally substituted by one or more identical or different halogen(s) and/or nitro group(s).

The compounds of formula (I) are pharmaceutically active, and are particularly useful in the veterinary therapy as anthelmintics. In addition they show pesticidal, particularly acaricidal, fungicidal and herbicidal properties. The invention relates also to pharmaceutical and pesticidal compositions containing as active ingredient compounds of formula (I).

The compounds of formula (I), in which the substituents are as defined, with the proviso that if $R^2$ is hydrogen and the substituent —$N(R,R^1)$ is in para-position related to the sulfoxide group, R and $R^1$ are other than hydrogen or methyl, are new.

8 Claims, No Drawings

NITRAMINODIARYL SULFOXIDE DERIVATIVES, PROCESS FOR THEIR PREPARATION AND PHARMACEUTICAL AND PESTICIDAL COMPOSITIONS CONTAINING THEM

The invention relates to a new process for the preparation of nitraminodiaryl sulfoxide derivatives. More particularly, the invention concerns a new process for preparing the partially new nitraminodiaryl sulfoxide derivatives of formula (I),

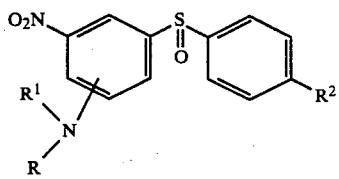

wherein
R and $R^1$ represent hydrogen or alkyl having from 1 to 6 carbon atoms, and
$R^2$ is hydrogen, halogen, alkyl having from 1 to 6 carbon atoms, alkoxy having from 1 to 6 carbon atoms or phenyl or thiophenyl both optionally substituted by one or more identical or different halogen(s) and/or nitro group(s).

According to the invention the nitraminodiaryl sulfoxide derivatives of formula (I), wherein R, $R^1$ and $R^2$ are as defined above, are prepared by reacting a nitrodiaryl sulfoxide derivative of the formula (II),

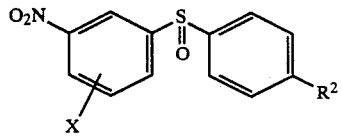

wherein
$R^2$ is as defined above, and
X is halogen or alkoxy having from 1 to 6 carbon atoms,
with an amine derivative of the formula (III),

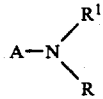

wherein
R and $R^1$ are as defined above, and
A is hydrogen or a group —CO—$R^3$, in which
$R^3$ is hydrogen, alkyl having from 1 to 6 carbon atoms or a group —N(R, $R^1$), in which R and $R^1$ are as defined above,
or a salt thereof.

In the above formulae X and $R^2$ as halogen represent fluorine, chlorine, bromine or iodine, preferably chlorine, while as an alkoxy having from 1 to 6 carbon atoms they stand for a straight-chained or branched alkoxy, such as methoxy, ethoxy, n-propoxy, isopropoxy, n-butoxy, sec.-butoxy, ter.-butoxy, isobutoxy, n-pentoxy, isopentoxy, n-hexyloxy, isohexyloxy, etc., preferably methoxy.

In the definition of $R^2$, R, $R^1$ and $R^3$ the term "alkyl having from 1 to 6 carbon atoms" is used to refer to straight-chained or branched alkyl groups, such as e.g. methyl, ethyl, n-propyl, isopropyl, n-butyl, isobutyl, sec.-butyl, tert.-butyl, n-pentyl, isopentyl, n-hexyl and isohexyl groups.

The compounds of formula (I) are pharmaceutically active, which can particularly be useful in the veterinary therapy as anthelmintics; and they show pesticidal, particularly acaricidal, fungicidal and herbicidal properties.

The compounds of formula (I) are further valuable intermediates in the preparation of other new and known bioactive aromatic sulfoxide derivatives, such as benzimidazole and substituted diamino sulfoxides having anthelmintic and fungicidal activity, e.g. Oxfendazol [5-(6)-phenylsulfinyl-2-carbomethoxyaminobenzimidazole]. These can be prepared from the compounds according to the invention by reduction and coupling with a carbamic acid ester derivative.

Compounds of formula (I), in which the group —N($R^1$R) is in para-position with respect to the sulfoxide group, $R^2$ is hydrogen, R and $R^1$ are identical and stand for hydrogen or methyl are known, while the other compounds of formula (I) are new.

Of the compounds of formula (I), those in which $R^2$, R and $R^1$ each stands for hydrogen are disclosed in the German Patent Specifications Nos. 2,462,258 and 2,549,417, and are prepared by nitrating the corresponding 4-aminodiaryl sulfoxide. To avoid the oxidative side-reactions, in this process the amino groups should be protected by acylation and after the nitration the acylamino-nitro-diaryl sulfoxide obtained has to be desacylated. Therefore, the process, which would normally include only a nitration step, includes two additional reaction steps, i.e. becomes a three-step procedure. A further disadvantage of this process is that it yields a mixture of isomeric nitro-compounds, and the nitration is carried out with a mixture of foaming nitric acid and a small amount of concentrated sulfuric acid in an acetic acid medium containing acetic anhydride, which is highly explosive due to the formation of acetyl nitrate, especially when performed on industrial scale.

Compounds of formula (I), in which $R^2$ is hydrogen and R and $R^1$ are methyl are prepared according to Ann. Chim. (Rome), 60(7), 527–536 [Ref.: C.A. 74 (11), 53202B] by treating the corresponding diphenyl sulfides with nitric acid in nitromethane. Due to the use of the highly aggressive and dangerous nitric acid, in this process a substantial amount of by-product is formed as a result of the splitting of the bond between the sulfur atom and phenyl group; consequently the yield is reduced and the product obtained will be contaminated.

We have surprisingly found that by using as a starting material instead of 4-aminodiaryl sulfoxides halogen- or alkoxy-substituted nitrodiaryl sulfoxides of the formula (II), the desired compounds can be obtained with an excellent yield, in a high purity, since both the halogen and the alkoxy group in a compound of formula (II) can efficiently be replaced by a suitable amine group. The reaction involves a very simple, single reaction step, proceeds without undesired side-reactions and can be carried out even on industrial scale without special safety measures.

Starting compounds of the formula (II) are new and are prepared as disclosed in our copending patent application corresponding to the Hungarian application No. 813/84 corresponding to the concurrently filed copending application Ser. No. 706,704. They can for example be prepared by reducing an arylsulfonyl halide with an alkali metal sulfite, treating the arylsulfinate obtained with a strong mineral acid, treating the arylsulfinic acid or the unchanged arylsulfinate with a halogenating agent and finally reacting the arylsulfinyl halide obtained with a benzene derivative, in the presence of a catalyst of the Lewis acid type. Compounds of the formula (II) are obtained by this process in a high purity, with an excellent yield, and the process is easy to perform even on industrial scale.

In the process according to the invention as a compound of formula (III) for example ammonia, preferably as an aqueous solution, an aliphatic primary amine, such as methylamine, ethylamine, n-propylamine, isopropylamine, n-butylamine, sec.-butylamine, tert.-butylamine, etc., an aliphatic secondary amine, such as dimethylamine, diethylamine, diisopropylamine, dibutylamine, etc., an aliphatic monocarboxylic acid amide, e.g. formic acid amide, acetic acid amide, propionic acid amide, dimethyl formamide, etc., or carbonic acid amides, such as urea, ammonium salts, such as ammonium chloride, ammonium carbonate, etc. are used.

The process according to the invention is carried out in an organic solvent, for example a mono- or polyfunctional aliphatic alcohol having from 1 to 8 carbon atoms, such as ethylene glycol, glycerine, diethylene glycol, their water-miscible monoalkyl esters, e.g. cellosolve, or other cyclic ethers, e.g. dioxane or tetrahydrofurane, etc. or in a mixture of any of these solvents with water. The reaction is preferably performed in a (1:4)–(4:1) mixture of an aliphatic alcohol and water. The reaction temperature is generally between 70° C. and 200° C., preferably 80° C. and 120° C., i.e. the reaction proceeds under very mild conditions, therefore practically is devoid of side reactions. This is very important since during animation reactions one generally has to count on side-reactions, such as the splitting off of sulfinic acid in the instant case, or the hydrolytic substitution of the halogen atom or alkoxy group. These theoretically possible reactions do, however, not take place in the process according to the invention. The process is preferably carried out using 2.0 to 50, preferably 2.5 to 20 moles of the compound of formula (III) or a salt thereof, related to one mole of a compound of formula (II).

The reaction mixture according to the invention is treated in a conventional manner. The product is generally obtained with a high yield, in a pure, crystalline form.

The compounds of the formula (I), if desired, can be subjected to further purification, e.g. recrystallization. The solvents used for recrystallization are selected depending on the solubility and crystallization properties of the compound to be crystallized.

As mentioned before, compounds of the formula (I),

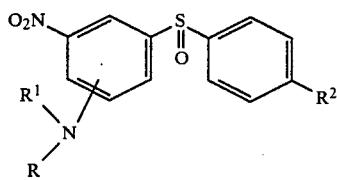

in which

R and $R^1$ are hydrogen or alkyl having from 1 to 6 carbon atoms, and $R^2$ is hydrogen, halogen, alkyl having from 1 to 6 carbon atoms, alkoxy having from 1 to 6 carbon atoms, or phenyl or phenylthio optionally substituted by one or more identical or different halogen(s) and/or nitro group(s), with the proviso that if $R^2$ is hydrogen and the substituent —N(R, $R^1$) is in para-position related to the sulfoxide group, R and $R^1$ are other than hydrogen or methyl, are new. The invention relates also to these compounds.

According to a still further aspect of the invention there are provided pharmaceutical compositions comprising as active ingredient at least one compound of formula (I), in which R, $R^1$ and $R^2$ are as defined above, without the proviso, in association with pharmaceutical carriers and/or excipients.

The invention further relates to pesticidal compositions comprising as active ingredient at least one compound of formula (I), wherein R, $R^1$ and $R^2$ are as hereinbefore defined, without the proviso, in association with conventional carriers and optionally further additives.

The preferred pharmaceutical and pesticidal compositions include the new compounds of formula (I), as hereinbefore defined.

The compounds of formula (I) may be formulated for therapeutic purposes. Carriers conventional for this purpose and suitable for parenteral or enteral administration as well as other additives may be used. As carriers solid or liquid compounds, for example water, gelatine, lactose, starch, pectin, magensium stearate, stearic acid, talc, vegetable oils, such as peanut oil, olive oil, arabic gum, polyalkylene glycols, and vaseline (registered Trade Mark), can be used. The compounds can be formulated as conventional pharmaceutical formulations, for example in a solid (globular and angular pills) or liquid (injectable oily or aqueous solutions or suspensions) form. The quantity of the solid carrier can be varied within wide limits, but preferably is between 25 mg. and 1 g. The compositions optionally contain also conventional pharmaceutical additives, such as preserving agents, wetting agents, salts for adjusting the osmotic pressure, buffers, flavoring and aroma substances.

The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For use as pesticides, the compounds of the formula (I) are formulated as conventional formulations, e.g. solutions, emulsions, soluble powders, suspensions, powder compositions, aerosol compositions, suspension and emulsion concentrates, powders for seed dressing. The compounds can be used for impregnating natural and synthetic materials, may be formulated as microcapsules, using polymeric substances and materials suitable for coating seeds, or can be converted into formulations supplied with a burnable filling, such as smoke patrons, boxes, spirals, and warm or cold fog compositions, which may be applied by ULV (ultra-low-volume) technique.

The pesticidal compositions can be prepared in a manner known per se, for example by admixing the active ingredients with carriers, i.e. liquid solvents, liquified gases under pressure and/or solid carriers. If desired, also surfactants, emulsifying and/or dispersing and/or foaming agents can be added to the system. If water is used as a carrier, as a co-solvent organic solvents may also be employed. The liquid solvents essentially include aromatic compounds such as xylene, toluene or alkylnaphthalenes; chlorinated aromatic or chlorinated aliphatic hydrocarbons such as chlorobenzene, chloroethylene or methylene chloride; aliphatic hydrocarbons, such as cyclohexane or paraffins such as mineral oil fractions, as well as alcohols such as butanol or glycol and the ethers and esters thereof; ketones such as acetone, methyl ethyl ketone, methyl isobutyl ketone or cyclohexanone; strongly polar solvents such as dimethyl formamide, dimethyl sulfoxide and water. Under liquidified gaseous carriers for example aerosol propellants such as halogenated hydrocarbons, butane, propane, nitrogen and carbon dioxide are meant. As solid carriers for example natural fossil meals, e.g. caoline, clay earth, talc, chalkstone, quartz, attapulgite, montmorillonite or diatomaceous earth, and synthetic fossil meals such as highly dispersed silicic acid, alumina and silicates are employed. As carriers for granulates for example broken and fractionated natural rocks, e.g. calcite, marbel, pumice, sepiolite, dolomite, and granulates of inorganic and organic meals, as well as granulates prepared from organic materials such as sawdust, coconut shell, corn husk and tobacco stems can be used. As emulsifying agents and/or foaming agents non-ionic emulsifiers such as polyoxyethylene fatty acid ethers, polyoxyethylene fatty alcohol ethers, e.g. alkylarylpolyglycol ether, alkylsulfonates, alkylsulfates, arylsulfonates and protein hydrolysates, while as dispersing agents e.g. lignine, sulfite waste liquors and methyl cellulose may be employed.

The pesticidal compositions according to the invention may contain also adhesives such as carboxymethyl cellulose, natural and synthetic, powdery, granular or latex-like polymers, e.g. acacia gum, polyvinyl alcohol, polyvinyl acetate, etc.

The pesticidal compositions according to the invention may further contain various pigments such as inorganic pigments, e.g. iron oxide, titanium dioxide, ferrocyane blue and organic pigments, e.g. alizarine, azometal phthalocyanine pigments, as well as micronutrients, e.g. iron, manganese, boron, copper, cobalt, molybdenum and zinc salts.

The pesticidal compositions generally contain 0.1 to 95% by weight, preferably 0.5 to 90% by weight of active ingredient.

The active ingredients may be applied in the form of commercial formulations and/or ready-to-use formulations prepared therefrom.

The active ingredient concentration of the ready-to-use formulations prepared from the compositions may vary within wide limits, and generally is between 0.000 000 1 and 95% by weight, preferably 0.01 and 10% by weight.

The route of application always depends on the specific formulation used.

The invention is elucidated in detail by the aid of the following non-limiting Examples.

EXAMPLE 1

Phenyl-(4-amino-3-nitrophenyl) sulfoxide 28.15 g. (0.1 mole) of phenyl-(4-chloro-3-nitrophenyl) sulfoxide are admixed with 76.5 ml. (0.9 moles) of an aqueous ammonium hydroxide solution having a concentration of 20 g./100 ml. and 93.5 ml. of isopropanol. The reaction mixture is heated up to 100° C. and the conversion grade of amination is controlled by gas chromatography or high pressure liquid chromatography. After about 10 hours only about 2% of the starting material are present in the reaction mixture. This time the reaction mixture is slowly cooled to 30° to 40° C., whereupon 15 ml. of water are added under stirring, the mixture is stirred at room temperature for half an hour, filtered, the solid remaining on the filter is washed with water and dried.

25.3 g. of phenyl-(4-amino-3-nitrophenyl) sulfoxide are obtained as a yellow crystalline material.

Purity: 98% (determined by high pressure liquid chromatography)

Melting point: 146° to 147° C.

Yield: 95% of theoretical.

EXAMPLE 2

Phenyl-(4-amino-3-nitrophenyl) sulfoxide 27.7 g. (0.1 moles) of phenyl-(4-methoxy-3-nitrophenyl) sulfoxide are admixed with 76.5 ml. (0.9 moles) of an aqueous ammonium hydroxide solution having a concentration of 20 g./100 ml. and 93.5 ml. of isopropanol. The reaction mixture is kept at 100° C. for 16 hours. As a result, the concentration of the starting material in the reaction mixture decreases below 2%.

The reaction mixture in further treated as described in Example 1. 25 g. of the aimed compound are obtained.

Purity: 98%

Melting point: 146° to 147° C.

Yield: 93.5% of theoretical.

EXAMPLE 3

Phenyl-(4-amino-3-nitrophenyl) sulfoxide

A mixture of 28.15 g. (0.1 mole) of phenyl-(4-chloro-3-nitrophenyl) sulfoxide, 45 g. 1.0 mole of formic acid amide, 94 ml. of isopropanol and 50 ml. of water is heated at 150° C. for 15 hours. The reaction mixture is further tested as described in Example 1.

22 g. of the desired compound are obtained.

Yield: 81% of theoretical

Melting point: 146° to 147° C.

EXAMPLE 4

Phenyl-(4-amino-3-nitrophenyl) sulfoxide

To a mixture of 80 ml. of ethylene glycol, 4 ml. of water and 28.15 g. (0.1 mole) of phenyl-(4-chloro-3-nitrophenyl) sulfoxide 60 g. (1.0 mole) of urea are added at 170° C., in about 2 hours, and the reaction mixture is stirred at this temperature for two hours. The progress of the reaction is monitored by thin layer chromatography (5:1 mixture of benzene and methanol, Alufolie Kieselgel 60 F$_{254}$, detecting by u.v. light). When the conversion is not complete, further 18 g. (0.3 moles) of urea are added to the reaction mixture portionwise, and the mixture is stirred at 170° C. for an additional hour. After the addition of 70 ml. of water the reaction mixture is treated as described in Example 1.

21 g. of phenyl-(4-amino-3-nitrophenyl) sulfoxide are obtained.

Yield: 77% of theoretical.

Melting point: 146° to 147° C.

EXAMPLE 5

Phenyl-(4-dimethylamino-3-nitrophenyl) sulfoxide

A mixture of 28.15 g. (0.1 mole) of phenyl-(4-chloro-3-nitrophenyl) sulfoxide, 150 g. (1.0 mole) of a 30% aqueous dimethyl amine solution and 150 ml. of isopropanol is heated at 120° C. for 6 hours, whereupon the reaction mixture is diluted with 100 ml. of water, and furtheron the procedure described in Example 1 is followed.

25.5 g. of phenyl-(4-dimethylamino-3-nitrophenyl) sulfoxide are obtained as a yellow crystalline substance.
Purity: 98%.
Melting point: 125° to 126° C.
Yield: 86% of theoretical.

EXAMPLE 6

Phenyl-(4-dimethylamino-3-nitrophenyl) sulfoxide

The procedure described in Example 5 is followed except that dimethyl amine is replaced by 73 g. (1.0 mole) of dimethyl formamide and 75 ml. of water. The reaction is carried out at 120° C. for 15 hours.

24 g. of the desired compound are obtained.
Yield: 81% of theoretical.
Melting point: 124° to 126° C.

EXAMPLE 7

(4-Amino-3-nitrophenyl)-4-methylphenyl sulfoxide

The procedure described in Example 1 is followed, except that as a starting material instead of phenyl-(4-chloro-3-nitrophenyl) sulfoxide a corresponding amount of (4-chloro-3-nitrophenyl)-4-methylphenyl sulfoxide is used.
Yield: 80%.
Melting point: 161° to 163° C.

EXAMPLE 8

(4-Amino-3-nitrophenyl)-4-chlorophenyl sulfoxide

The procedure described in Example 1 is followed, except that as a starting material instead of phenyl-(4-chloro-3-nitrophenyl) sulfoxide a corresponding amount of (4-chloro-3-nitrophenyl)-4-chlorophenyl sulfoxide is employed.
Yield: 77%.
Melting point: 176° to 179° C.

EXAMPLE 9

Phenyl-(2-amino-5-nitrophenyl) sulfoxide

The procedure described in Example 1 is followed, except that as a starting material instead of phenyl-(4-chloro-3-nitrophenyl) sulfoxide a corresponding amount of phenyl-(2-chloro-5-nitrophenyl) sulfoxide is employed, and the reaction is carried out at 140° C. for 20 hours.
Yield: 84%.
Melting point: 188° to 191° C.

EXAMPLE 10

4-(4-Amino-3-nitrophenyl-sulfinyl)-biphenyl

The procedure described in Example 1 is followed, except that as a starting material instead of phenyl-(4-chloro-3-nitrophenyl) sulfoxide a corresponding amount of 4-(4-chloro-3-nitrophenyl-sulfinyl)-biphenyl is employed.
Yield: 81%.
Melting point: 198° to 200° C.

EXAMPLE 11

[4-(4-Chloro-3-nitrophenylthio)-phenyl]-(4-amino-3-nitrophenyl) sulfoxide

The procedure described in Example 1 is followed, except that as a starting material instead of phenyl-(4-chloro-3-nitrophenyl) sulfoxide a corresponding amount of [4-(4-chloro-3-nitrophenylthio)-phenyl]-(4-chloro-3-nitrophenyl) sulfoxide is employed, and the amination is carried out at 110° C. for 20 hours. The product obtained is a mixture of two substances, which can be separated by chromatography.

The title compound is obtained with a yield of 65%; melting point: 170° to 172° C.

In addition [4-(4-amino-3-nitrophenylthio)-phenyl]-(4-amino-3-nitrophenyl) sulfoxide, melting at 200° to 202° C. is obtained, with a yield of 16%.

EXAMPLE 12

(4-Amino-3-nitrophenyl)-4-methoxyphenyl sulfoxide

The procedure described in Example 1 is followed except that as a starting material instead of phenyl-(4-chloro-3-nitrophenyl) sulfoxide a corresponding amount of (4-chloro-3-nitrophenyl)-4-methoxyphenyl sulfoxide is used.
Yield: 83%.
Melting point: 197° to 199° C.

EXAMPLE 13

(4-Amino-3-nitrophenyl)-4-fluorophenyl sulfoxide

The procedure described in Example 1 is followed, except that as a starting material instead of phenyl-(4-chloro-3-nitrophenyl) sulfoxide a corresponding amount of 4-fluorophenyl-(4-chloro-3-nitrophenyl) sulfoxide is employed.
Melting point: 169° to 171° C.
Yield: 85%.

EXAMPLE 14

(4-Amino-3-nitrophenyl)-4-bromophenyl sulfoxide

The procedure described in Example 1 is followed, except that as a starting material instead of phenyl-(4-chloro-3-nitrophenyl) sulfoxide a corresponding amount of 4-bromophenyl-(4-chloro-3-nitrophenyl) sulfoxide is employed.
Melting point: 202° to 205° C.
Yield: 87%.

EXAMPLE 15

(4-Ethylamino-3-nitrophenyl)-phenyl sulfoxide

A mixture of 28.15 g. (0.1 mole) of phenyl-(4-chloro-3-nitrophenyl) sulfoxide, 50 g. (0.515 moles) of a 46.4% methanolic ethylamine solution, 70 ml. of water and 50 ml. of ethanol is heated at 100° C. for 5.5 hours. The reaction mixture is then cooled to room temperature under stirring, stirred at room temperature for half an hour, filtered and the substance remaining on the filter is washed with water and dried.

25 g. of the desired compound are obtained as a yellow crystalline substance.
Yield: 86% of theoretical.
Melting point: 122° to 124° C.

EXAMPLE 16

(4-sec.-Butylamino-3-nitrophenyl)-phenyl sulfoxide

A mixture of 28.15 g. (0.1 mole) of phenyl-(4-chloro-3-nitrophenyl) sulfoxide, 58.4 g. (0.8 moles) of sec.-butylamine, 90 ml. of isopropanol and 50 ml. of water is heated at 100° C. for 6 hours. The reaction mixture is further treated as described in Example 15.

28 g. of the desired compound are obtained.
Yield: 88% of theoretical.
Melting point: 88° to 91° C.

EXAMPLE 17

(2-Amino-5-nitrophenyl)-4-chlorophenyl sulfoxide

The procedure described in Example 1 is followed, except that as a starting material instead of phenyl-(4-chloro-3-nitrophenyl) sulfoxide a corresponding amount of (2-chloro-5-nitrophenyl)-4-chlorophenyl sulfoxide is used and the reaction is performed at 140° C. for 2 hours.

EXAMPLE 18

1-(4-bromophenyl)-4-(4-amino-3-nitrophenyl-sulfinyl)-benzene

The procedure described in Example 1 is followed, except that as a starting material instead of phenyl-(4-chloro-3-nitrophenyl) sulfoxide a corresponding amount of 1-(4-bromophenyl)-4-(4-chloro-3-nitrophenylsulfinyl)benzene is used.

The desired compound is obtained with a yield of 82%.

Melting point: 218° to 220° C.

EXAMPLE 19

(4-Amino-3-nitrophenyl)-(4-methylthiophenyl) sulfoxide

The procedure described in Example 1 is followed, except that as starting material instead of phenyl-(4-chloro-3-nitrophenyl) sulfoxide a corresponding amount of (4-chloro-3-nitrophenyl)-4-methylthiophenyl sulfoxide is employed.

We claim:

1. An anthelmintic method of treatment which comprises the step of administering to a mammalian subject, a therapeutically effective amount of the compound of the Formula (I)

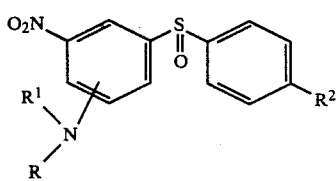

wherein
R and $R^1$ are hydrogen or $C_1$ to $C_6$ alkyl; and
$R^2$ is hydrogen, halogen, $C_1$ to $C_6$ alkyl, $C_1$ to $C_6$ alkoxy, or phenyl or phenylthio both optionally substituted by at least one halogen or nitro substituent.

2. The anthelmintic method of treatment defined in claim 1 wherein the compound of the Formula (I) is (4-chlorophenyl)-(3-nitro-4-aminophenyl)-sulfoxide.

3. An antifungal method of treatment which comprises the step of applying to the fungi a fungicidally effective amount of a compound of the Formula (I)

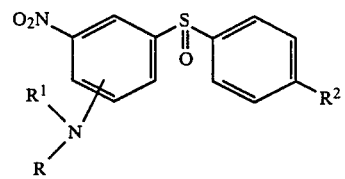

wherein
R and $R^1$ are hydrogen or $C_1$ to $C_6$ alkyl; and
$R^2$ is hydrogen, halogen, $C_1$ to $C_6$ alkyl, $C_1$ to $C_6$ alkoxy, or phenyl or phenylthio both optionally substituted by at least one halogen or nitro substituent.

4. The antifungal method of treatment defined in claim 3 wherein the compound of the Formula (I) is selected from the group consisting of:
  (a) (3-nitro-4-aminophenyl)-(4-methylphenyl)-sulfoxide,
  (b) (3-nitro-4-aminophenyl)-(4-chlorophenyl)-sulfoxide,
  (c) phenyl-(3-nitro-6-aminophenyl)-sulfoxide,
  (d) phenyl-(3-nitro-4-ethylaminophenyl)-sulfoxide,
  (e) (3-nitro-4-aminophenylsulfinyl)-biphenyl, and
  (f) (3-nitro-4-aminophenyl)-(4-fluorophenyl)1-sulfoxide.

5. An herbicidal method of treatment which comprises the step of applying to an undesired plant, a herbicidally effective amount of a compound of the Formula (I)

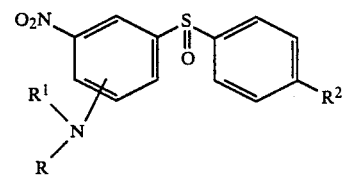

wherein
R and $R^1$ are hydrogen or $C_1$ to $C_6$ alkyl;
$R^2$ is hydrogen, halogen, $C_1$ to $C_6$ alkyl, $C_1$ to $C_6$ alkoxy, or phenyl or phenylthio both optionally substituted by at least one halogen or nitro substituent.

6. The herbicidal method of treatment defined in claim 5 wherein the compound of the Formula (I) is selected from the group consisting of:
  (a) (3-nitro-4-aminophenyl)-(4-fluorophenyl)-sulfoxide,
  (b) phenyl-(3-nitro-6-aminophenyl)-sulfoxide, and
  (c) phenyl-(3-nitro-4-ethylaminophenyl)-sulfoxide.

7. An acaricidal method of treatment which comprises the step of applying to an acarid an acaricidally effective amount of a compound of the Formula (I)

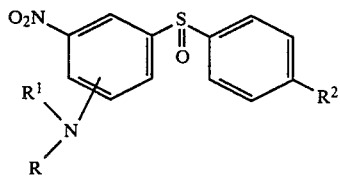

wherein
R and $R^1$ are hydrogen or $C_1$ to $C_6$ alkyl; and
$R^2$ is hydrogen, halogen, $C_1$ to $C_6$ alkyl, $C_1$ to $C_6$ alkoxy, or phenyl or phenylthio both optionally substituted by at least one halogen or nitro substituent.

8. The acaricidal method of treatment defined in claim 7 wherein the compound of the Formula (I) is selected from the group consisting of:
(a) phenyl-(3-nitro-6-aminophenyl)-sulfoxide,
(b) (3-nitro-4-aminophenyl-sulfinyl)-biphenyl,
(c) (3-nitro-4-aminophenyl-(4-methylphenyl)-sulfoxide,
(d) (3-nitro-4-aminophenyl-(4-fluorophenyl)-sulfoxide, and
(e) (3-nitro-4-aminophenyl-(4-chlorophenyl)-sulfoxide.

* * * * *